(12) United States Patent
Okerlund et al.

(10) Patent No.: US 7,565,190 B2
(45) Date of Patent: Jul. 21, 2009

(54) CARDIAC CT SYSTEM AND METHOD FOR PLANNING ATRIAL FIBRILLATION INTERVENTION

(75) Inventors: Darin R. Okerlund, Muskego, WI (US); Jasbir S. Sra, W305 N2963 Red Oak Ct., Pewaukee, WI (US) 53072; Helen Thomson, Milwaukee, WI (US)

(73) Assignees: GE Medical Systems Global Technology Company, LLC, Wankesha, WI (US); Jasbir S. Sra, Pewaukee, WI (US)

( * ) Notice: Subject to any disclaimer, the term of this patent is extended or adjusted under 35 U.S.C. 154(b) by 776 days.

(21) Appl. No.: 10/249,812

(22) Filed: May 9, 2003

(65) Prior Publication Data

US 2004/0225331 A1    Nov. 11, 2004

(51) Int. Cl.
*A61B 5/05* (2006.01)
(52) U.S. Cl. .................. 600/426; 600/427; 600/425; 600/424; 600/428; 600/407; 606/41; 382/128; 382/130; 382/131
(58) Field of Classification Search .............. 600/427, 600/374, 407, 424, 425–428, 410, 523; 606/41; 128/920, 922; 382/128, 130, 131
See application file for complete search history.

(56) References Cited

U.S. PATENT DOCUMENTS

| | | | |
|---|---|---|---|
| 3,954,098 A | 5/1976 | Dick et al. .................. 128/2.05 |
| 4,364,397 A | 12/1982 | Citron et al. | |
| 4,574,807 A | 3/1986 | Hewson et al. ........ 128/419 PG |
| 5,245,227 A | 9/1993 | Nowak et al. ................ 324/322 |
| 5,274,551 A | 12/1993 | Corby, Jr. .............. 364/413.13 |
| 5,304,212 A | 4/1994 | Czeisler et al. ............... 607/88 |
| 5,348,020 A | 9/1994 | Hutson ....................... 128/696 |
| 5,353,795 A | 10/1994 | Souza et al. ............. 128/653.2 |
| 5,391,199 A | 2/1995 | Ben-Haim .................. 607/122 |
| 5,431,688 A | 7/1995 | Freeman ...................... 607/10 |
| 5,515,849 A | 5/1996 | Murashita et al. | |
| 5,568,384 A | 10/1996 | Robb et al. ............ 364/419.13 |
| 5,738,096 A | 4/1998 | Ben-Haim ............... 128/653.1 |
| 5,765,561 A * | 6/1998 | Chen et al. .................. 600/407 |
| 5,823,958 A | 10/1998 | Truppe ........................ 600/426 |

(Continued)

FOREIGN PATENT DOCUMENTS

EP    1182619 A2    2/2002

(Continued)

OTHER PUBLICATIONS

PCT Search Report for PCT/US2004/020909.

(Continued)

*Primary Examiner*—Brian Casler
*Assistant Examiner*—John F Ramirez
(74) *Attorney, Agent, or Firm*—Cantor Colburn LLP

(57) ABSTRACT

A method for planning atrial fibrillation (AF) intervention for a patient includes obtaining acquisition data from a medical imaging system, and generating a 3D model of the left atrium and pulmonary veins of the patient. One or more left atrial anatomical landmarks are identified on the 3D model, and saved views of the 3D model are registered on an interventional system. One or more of the registered saved views are visualized with the interventional system.

16 Claims, 2 Drawing Sheets

U.S. PATENT DOCUMENTS

| | | | |
|---|---|---|---|
| 5,839,440 A | 11/1998 | Liou et al. | 128/654 |
| 5,951,475 A | 9/1999 | Gueziec et al. | 600/425 |
| 6,058,218 A | 5/2000 | Cline | |
| 6,081,577 A | 6/2000 | Webber | 378/23 |
| 6,154,516 A | 11/2000 | Heuscher et al. | 378/15 |
| 6,208,347 B1 | 3/2001 | Migdal | 345/419 |
| 6,233,304 B1 | 5/2001 | Hu et al. | 378/8 |
| 6,235,038 B1 | 5/2001 | Hunter et al. | 606/130 |
| 6,246,898 B1 | 6/2001 | Vesely | 600/424 |
| 6,249,693 B1 | 6/2001 | Cline et al. | 600/410 |
| 6,252,924 B1 | 6/2001 | Davantes et al. | 378/8 |
| 6,256,368 B1 | 7/2001 | Hsieh et al. | 378/8 |
| 6,266,553 B1 | 7/2001 | Fluhrer et al. | 600/428 |
| 6,289,115 B1 | 9/2001 | Takeo | 382/130 |
| 6,289,239 B1 | 9/2001 | Panescu et al. | 600/523 |
| 6,314,310 B1 | 11/2001 | Ben-Haim et al. | 600/424 |
| 6,325,797 B1 | 12/2001 | Stewart et al. | 606/41 |
| 6,348,793 B1 | 2/2002 | Balloni et al. | 324/309 |
| 6,353,445 B1 | 3/2002 | Babula et al. | 345/733 |
| 6,381,485 B1 | 4/2002 | Hunter et al. | 600/407 |
| 6,389,104 B1 | 5/2002 | Bani-Hashemi et al. | 378/98.12 |
| 6,411,848 B2 | 6/2002 | Kramer et al. | 607/9 |
| 6,421,412 B1 | 7/2002 | Hsieh et al. | 378/9 |
| 6,456,867 B2 | 9/2002 | Reisfeld | 600/407 |
| 6,468,265 B1 | 10/2002 | Evans et al. | 606/1 |
| 6,490,475 B1 | 12/2002 | Seeley et al. | 600/426 |
| 6,490,479 B2 | 12/2002 | Bock | 600/518 |
| 6,504,894 B2 | 1/2003 | Pan | 378/8 |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1 | 11/2003 | Keidar | 600/424 |
| 6,782,284 B1 | 8/2004 | Subramanyan et al. | 600/407 |
| 6,950,689 B1* | 9/2005 | Willis et al. | 600/407 |
| 7,047,060 B1 | 5/2006 | Wu | |
| 2002/0010392 A1 | 1/2002 | Desai | 600/374 |
| 2002/0042570 A1 | 4/2002 | Schaldach et al. | |
| 2002/0046756 A1 | 4/2002 | Laizzo et al. | 128/899 |
| 2002/0138105 A1 | 9/2002 | Kralik | 607/9 |
| 2003/0018251 A1* | 1/2003 | Solomon | 600/427 |
| 2003/0023266 A1 | 1/2003 | Borillo et al. | 606/200 |
| 2003/0028183 A1 | 2/2003 | Sanchez et al. | 606/34 |
| 2003/0097219 A1 | 5/2003 | O'Donnell et al. | 702/19 |
| 2003/0120264 A1 | 6/2003 | Lattouf | |
| 2003/0187358 A1 | 10/2003 | Okerlund et al. | 600/443 |
| 2003/0220557 A1 | 11/2003 | Cleary et al. | 600/409 |
| 2004/0027347 A1 | 2/2004 | Farsaie | 345/419 |
| 2004/0087850 A1 | 5/2004 | Okerlund et al. | 600/407 |
| 2004/0225212 A1 | 11/2004 | Okerlund et al. | 600/407 |
| 2004/0225328 A1 | 11/2004 | Okerlund et al. | 607/9 |

FOREIGN PATENT DOCUMENTS

| | | |
|---|---|---|
| EP | 1321101 A2 | 12/2002 |
| WO | WO 91/07726 | 5/1991 |
| WO | WO 96/10949 | 4/1996 |

OTHER PUBLICATIONS

F. H.M. Wittkampf et al.; "Loca Lisa—New Technique for Real-Time 3-Dimensional Localization of Regular Intracardiac Electrodes;" *Circulation*h; 1999; 99:1312-1317.

"Advanced Vessel Analysis" product descritpoin, [online] http://www.gehealthcare.com/usen/ct/clin_app/products/aswessel.html [retrieved Dec. 1, 2004].

"CardilQ" product description, [online], http://egems.gehealtcare.com/geCommunity/Europe/flex_trial/awFlexTrial/aw3_1/eflextrial [retrieved Dec. 1, 2004].

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Rhythm;" *Circulation* 1998; 98:997-98.

C. C. Gornick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Ekectrophysiol*, Dec. 2002, 25(12):1699-707.

F. Wittkampf et al., "Real-Time, Three-Dimensional, Nonfluoroscopic Localization of the Lasso Catheter;" *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven. Cardiac Electrophysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N Engl. J. Med*. 2001; 344-873-880.

M. V. Pitzalis et al., "Cardiac Resynchronization Therapy Tailored by Echocardiographic Evaluation of Ventricular Acnchrony;" *J. Am. Coll. Cardiol*. 2002; 40:1615-22.

W. T. Abraham et al., "Cardiac Resynchronization in Chronic Heart Failure;" *N. Eng. J. Med*. 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab*. 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clincal Applications;" *American Society of Neuroimaging*; 2000; 10:39-46.

S. A. Ben-Haim et al.; "Nonfluoroscopic, in vivo navigation and mapping technology;" *Nature Medicine*; 1996; 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;" J. Am. Coll. Cardiol 2001; 38:1-47.

D. R. Ney "Volumetric Rendering of Computed Tomography Data: Principles and Techniques;" *IEEE Computer Graphics and Applications*; 1990; 24-32.

N. M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quaility Considerations;" *Computed Body Tomography*, 1998, Lippincot-Raven, Philadelphia, PA pp. 1-20.

Milan Sonka and J. Michael Fitzpatrick (eds); *Handbook of Medical Imaging Vol. 2. Medical Image Processing and Analysis*; pp. 129-174 & 447-506.

W. M. Feinberg et al.; "Prevalence, Age Distribution, and Gender of Patients with Atrial Fibrillation;" *Arch. Intern. Med. vol. 155*; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrillation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology- Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

W. M. feinberg, J. L. Blackshear, A. Laupacis, R. Kronmal, and R. G. Hart; "Prevalence, Age Distribution, and Gender of Patients with Atrial Fibrillation;" Arch Intern Med., vol. 155, Mar. 13, 1995; pp. 469-473.

"Current Problems in Cardiology- Atrial Fibrilliation: Epidemiology, Mechanisms, and Management;" Current Problems in Cardiology, Jul. 2000; pp. 406-524.

Sra et al., "Registration of Three-Dimensional Left Atrial Computed Tomographic Images With Projection Images Obtained Using Fluoroscopy", Circulation 2005; 112: 3763-3768.

"Tiny Device Blocks Unless Part of Heart, Prevents Blood Clots," Apr. 9, 2002; found at www.americanheart.org/presenter.jhtml?identifier=3001890.

"Operating in 3-D," Harvard Medical Alumni Bulletin, Ellen Barlow, found at www.med.harvard.edu/publications/HMAB/196fo3d.html.

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography IEEE Transactions on Medical Imaging, 21 (9): pp. 1059-68, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

* cited by examiner

CARDIAC CT SYSTEM AND METHOD FOR PLANNING ATRIAL FIBRILLATION INTERVENTION

BACKGROUND OF THE INVENTION

The present disclosure relates generally to cardiac implant systems and, more particularly, to a cardiac imaging system and method for planning atrial fibrillation intervention.

Atrial fibrillation (AF) is an arrhythmia in which the atria (upper chambers of the heart) stop contracting as they fibrillate, and is the most common of heart rhythm problems. It is estimated that over 2.2 million Americans have AF. Because of the role of the pulmonary veins (PVs) in generating AF, a variety of surgical and catheter techniques have been used to isolate the PVs from the left atrium using energy sources such as radiofrequency (RF) energy. In addition to PV isolation, several other strategic targets, such as the mitral valve to left inferior PVs, can be targeted to improve efficacy. Transmural lesions formed during ablation are advantageous, as discontinuous lines may allow AF breakthrough or potential development of other arrhythmias such as atrial flutter.

In unipolar systems, where the patient is grounded by an indifferent electrode applied to the skin (usually the back), current flows from the tip of the RF catheter and resistively heats tissue at the catheter tip contact. Deeper tissue planes are heated by conduction from the region of volume heating. Locally, temperatures above 100" C can occur causing tissue vaporization and surface charring which could be disastrous in areas such as the inside of the PVs. RF current producing temperatures from about 70to 80" C result in lesions about 3 to 6 mm deep. However, even temperatures above 50" C are also likely to cause PV stenosis. In studies of the anatomy of the PVs, a significant diversity of muscle fiber orientation is seen around the PVs. It is generally not known how muscle thickness varies in other strategic areas such as the mitral valve to left inferior PVs.

In a typical AF ablation procedure, the location(s) of premature atrial beats which act as triggers for initiation of AF is identified. However, such identification is possible in only a few patients. Then, circular catheters with multiple electrodes are placed inside the PVs. Using a second catheter, the ablation is then performed at sites suggesting conduction between the left atrium (LA) and the PVs. In addition to the previously mentioned problems, additional problems associated with AF ablation include the complex 3D geometry of the left atrium and PVs, as well as the variable muscle thickness and orientation of fibers in and around the PVs. These features make it difficult to appropriately target the areas of interest. As such, it would be desirable to be able to provide information, such as muscle thickness at and around the pulmonary veins and other strategic locations to improve the efficacy of an AV ablation procedure.

BRIEF DESCRIPTION OF THE INVENTION

The above discussed and other drawbacks and deficiencies of the prior art are overcome or alleviated by a method for planning atrial fibrillation (AF) intervention for a patient. In an exemplary embodiment, the method includes obtaining acquisition data from a medical imaging system, and generating a 3D model of the left atrium and pulmonary veins of the patient. One or more left atrial (LA) and pulmonary vein (PV) anatomical landmarks are identified on the 3D model, and saved views of the 3D model are registered on an interventional system. One or more of the registered saved views are visualized with the interventional system.

In another aspect, a method for planning atrial fibrillation (AF) intervention for a patient includes obtaining acquisition data from a medical imaging system using a protocol directed toward the left atrium and pulmonary veins. The acquisition data is segmented using a 3D protocol so as to visualize the left atrium and pulmonary veins. A 3D model of the left atrium and pulmonary veins of the patient is generated, and one or more left atrial (LA) and pulmonary vein (PV) anatomical landmarks on the 3D model are identified. Saved views of the 3D model are registered on an interventional system, and one or more of the registered saved views are visualized the interventional system. Levels of ablation to be applied to a specific area of one or more LA and PV surfaces are identified from the 3D model.

In still another aspect, a method for planning atrial fibrillation (AF) intervention for a patient includes obtaining acquisition data from a cardiac computed tomography (CT) imaging system using a protocol directed toward the left atrium and pulmonary veins. The acquisition data is segmented using a 3D protocol so as to visualize the left atrium and pulmonary veins. A 3D model of the left atrium and pulmonary veins of the patient is generated, and one or more left atrial (LA) and pulmonary vein (PV) anatomical landmarks on the 3D model are identified. Saved views of the 3D model are registered on a fluoroscopy system, and one or more of the registered saved views are visualized with the fluoroscopy system. Levels of ablation to be applied to a specific area of one or more LA and PV surfaces are identified from the 3D model.

In still another aspect, a system for planning atrial fibrillation (AF) intervention for a patient includes a medical imaging system for generating acquisition data, and an image generation subsystem for receiving the acquisition data and generating one or more images of the left atrium and pulmonary veins of the patient. An operator console is configured for identifying one or more left atrial (LA) and pulmonary vein (PV) anatomical landmarks on the one or more images, and a workstation includes post processing software for registering saved views of the 3D model on an interventional system. The interventional system is configured for visualizing one or more of the registered saved views therewith and identifying levels of ablation to be applied to a specific area of one or more LA and PV surfaces.

In still another aspect, a system for planning atrial fibrillation (AF) intervention for a patient includes a cardiac computed tomography (CT) imaging system for generating acquisition data, the CT imaging system using a protocol directed toward the left atrium and pulmonary veins. An image generation subsystem receiving the acquisition data and generates one or more images of the left atrial (LA) and pulmonary vein (PV) and pulmonary veins of the patient. The image generation system is further configured for segmenting the acquisition data using a 3D protocol so as to visualize the left atrium and pulmonary veins. An operator console is configured for identifying one or more left ventricle anatomical landmarks on the one or more images, and a workstation includes post processing software for registering saved views of the 3D model on a fluoroscopy system. The fluoroscopy system is configured for visualizing one or more of the registered saved views therewith and identifying levels of ablation to be applied to a specific area of one or more LA and PV surfaces.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a cardiac imaging system and method for atrial fibrillation (AF) ablation that provides information for planning interventional procedures that enable an electrophysiologist, cardiologist and/or surgeon to plan in advance a desired approach to take for the procedure. Additionally, with a more detailed three-dimensional (3D) geometrical representation of the left atrium (LA) and pulmonary veins (PV), as may be obtained from imaging modalities such as computed tomography (CT), magnetic resonance (MR) and ultrasound, the practitioner can identify the location and orientation of PVs and muscle thickness in and around the PV ostium, as well as at other strategic locations. The degree and location of applied RF energy may be selected beforehand so as to avoid the problems encountered with ablation procedures, thereby making the procedure more efficacious and reducing the risk of complications such as PV stenosis.

Although the exemplary embodiments illustrated hereinafter are described in the context of a CT imaging system, it will be appreciated that other imaging systems known in the art are also contemplated with regard to planning LA ablation.

Figure 1:
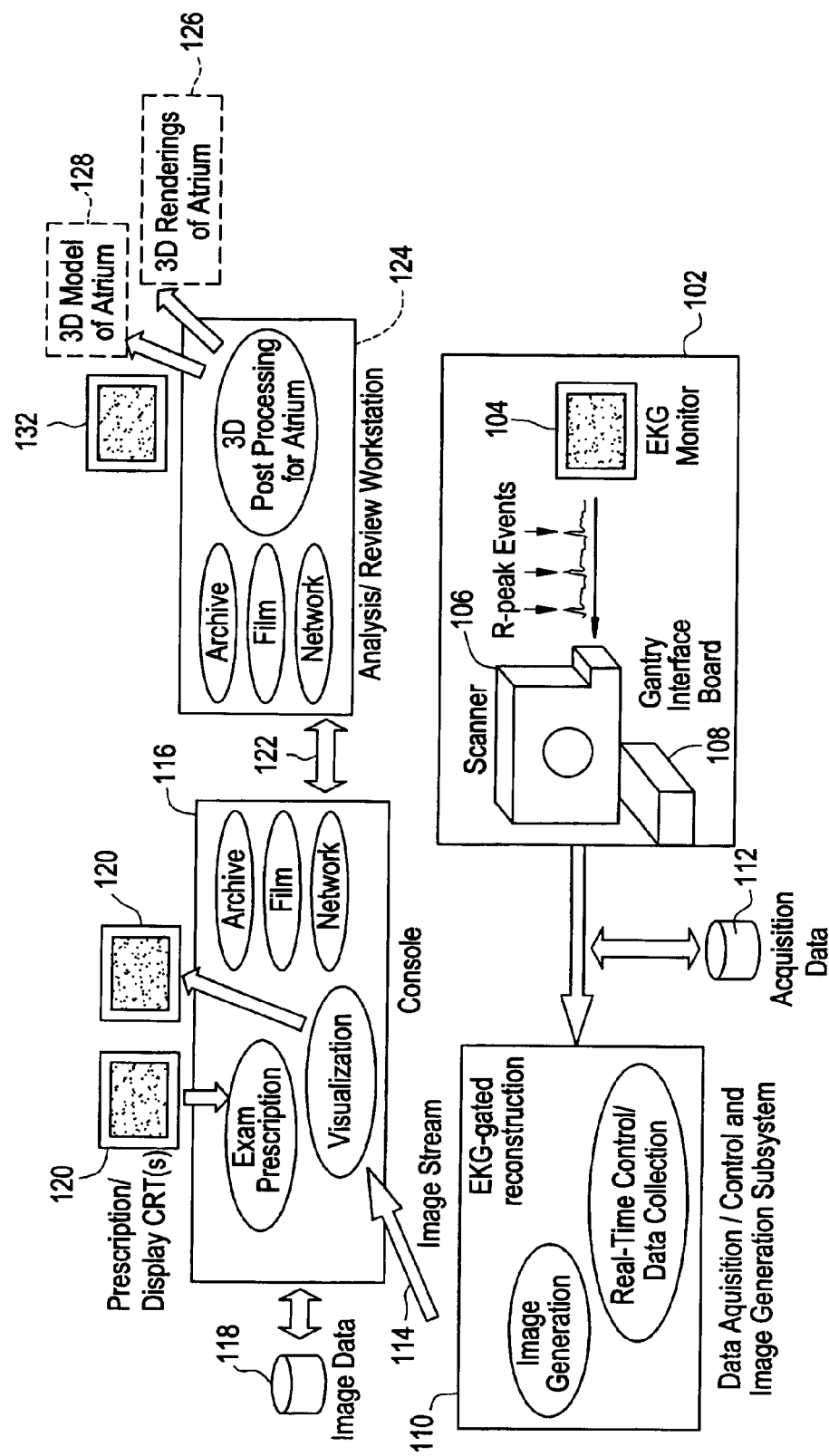
FIG. 1 is a schematic diagram of a medical imaging system, such as a computed tomography (CT) system, suitable for planning left atrial appendage isolation, in accordance with an embodiment of the invention.

Referring initially to FIG. 1, there is shown an overview of an exemplary cardiac computed tomography (CT) system 100 with support for cardiac imaging. Again, it should be understood that the cardiac CT system 100 is presented by way of example only, since other imaging systems known in the art (e.g., magnetic resonance, ultrasound) may also be used in an embodiment of the present invention. A scanner portion 102 of the system 100 includes an electrocardiographic (EKG) monitor 104 that outputs R-peak events into a scanner 106 through a scanner interface board 108. A suitable example of a scanner interface board 108 is a Gantry interface board, and can be used to couple an EKG system to the scanner. The cardiac CT subsystem defined by scanner portion 102 utilizes EKG-gated acquisition or image reconstruction capabilities to image the heart free of motion in its diastolic phase, as well as in multiple phases of systole and early diastole.

Data is outputted from the scanner portion 102 into a subsystem 110 that includes software for performing data acquisition, data control and image generation. In addition, data that is outputted from the scanner 106, including R-peak time stamps, is stored in an acquisition database 112. Acquisition is performed according to one or more acquisition protocols that are optimized for imaging the heart and specifically the left atrium and pulmonary veins. Image generation is performed using one or more optimized 3D protocols for automated image segmentation of the CT image dataset for the inner and outer surfaces of the LA. The automated procedure may require one or more queues from the operator, e.g., anteroposterior, left anterior oblique, and right anterior oblique views.

The image data stream 114 is sent to an operator console 116. The data used by software at the operator console 114 for exam prescription and visualization is stored in an image database 118, along with the data from the image data stream 114. Display screens 120 are provided to the operator of the exam prescription and visualization processes. The image data may be archived, put on film or sent over a network 122 to a workstation 124 for analysis and review, including 3D post processing. The post processing software depicted in the workstation 124 provides "immersible" views of the ostium of the LA and PVs, which can be visualized from the inside. These special views can be saved and viewed by the practitioner.

The 3D protocols of the post processing software enable the software to provide the certain quantitative features of the LA, such as contour, position orientation and thickness. These features may be provided automatically or semiwith user input and interaction, and saved into 3D rendering files 126 for use by the practitioner for interventional planning and procedure. The post processing software also provides for the export of detailed 3D models 128 of the left atrium and pulmonary veins. The 3D models 128 (which may be viewed on display screen 132 associated with workstation 124) are configured to include geometric markers inserted into the volume at landmarks of interest such that the PV ostial areas and the other strategic areas can be visualized as opaque markers with the left atrium, and the remainder of the PVs visualized in a translucent fashion.

In addition, the 3D models 128 may be in exported in any of several formats, including but not limited to: a wire mesh geometric model, a set of surface contours, a segmented volume of binary images, and a DICOM (Digital Imaging and Communications in Medicine) object using the radiation therapy (RT) DICOM object standard or similar object. Other formats known in the art can also be used to store and export the 3D models 128.

Figure 2:
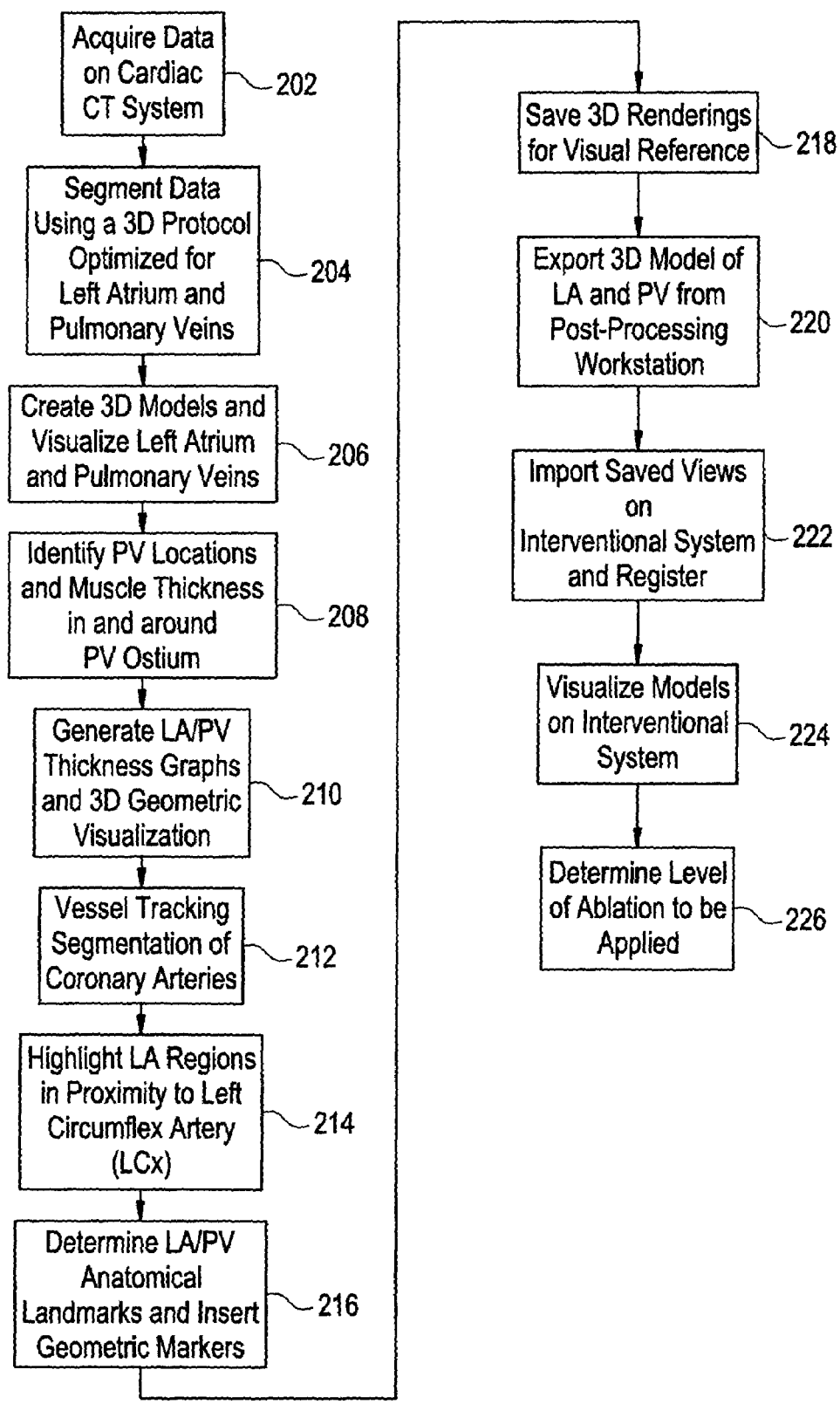
FIG. 2 is a flow diagram of a method for planning left atrial appendage isolation, in accordance with a further embodiment of the invention.

Referring now to FIG. 2, there is shown a flow diagram 200 illustrating a method for planning AF ablation, in accordance with a further embodiment of the invention. Beginning at block 202, a volume of data is initially acquired on the cardiac CT system, using a protocol that is preferably optimized for the left atrium (LA) pulmonary veins (PV) of the heart. At block 204, the image dataset is segmented with post-processing software using a 3D protocol optimized for the left atrium and pulmonary veins and preferably designed to extract the surfaces of the left atrium. Automated procedures may be employed, where appropriate, with or without queues from the operator (e.g., location of anteroposterior, left anterior oblique, posterolateral, oblique and right anterior oblique views).

Then, as shown in block 206, the LA and PVs are visualized using 3D surface and/or volume rendering to create 3D models of the LA and PVs, which also preferably includes an immersible view (i.e., a view from inside the chamber). In this manner, the PV locations may be identified and the muscle thickness in and around the PV ostium determined, as is illustrated at block 208. This information, in turn, may used to generate thickness graphs or plots, and 3D geometric visualization for quick analysis, as shown in block 210.

Proceeding to block 212, the image data set is further processed so as to perform vessel-tracking segmentation of the coronary arteries. A translucent 3D rendering of the LA/PVs is created along with (and in contrast to) an opaque rendering of the coronary arteries. In particular, those areas of the LA in proximity to the left circumflex artery (LCx) are highlighted, as excessive ablation of those areas could cause significant complications. This is indicated at block 214. Furthermore, the LA/PV thickness and coronary artery proximity data may be optionally translated into a 3D map that indicates (by spectral coloring, for example) the level of ablation to be applied to a given area of the LA/PV surface.

As shown in block 216, explicit geometric markers are inserted into the volume at landmarks of interest, wherein the markers may be subsequently visualized in a translucent fashion. Then, as illustrated at block 218, specific 3D renderings and axial images (such as DICOM images, video clips, films, multimedia formats, etc.) are saved as desired for subsequent visual reference during the interventional planning and for use during the interventional procedure. The saved views are then exported from the post-processing workstation (block 220) imported and registered with the projection image on the fluoroscopy system or alternatively, with the tomosynthesis images of the 3D fluoroscopy system, as shown in block 222.

The interventional system is accessed and the imported registered models therewith are visualized by the practitioner, as shown in block 224. Finally, at block 226, the practitioner determines the level of ablation to be applied. It will be appreciated that automatic techniques may be employed to perform any of the above steps by using one or more of the several computer-assisted detection, localization and visualization methods available. Moreover, these methods could, be completely automatic when the procedure and the organ of interest is specified or partly interactive with input from the user.

It will further be appreciated that through the use of the above described method and system embodiments, the planning of LA ablation is improved in that the imaging information generated and registered allows for an appropriately tailored approach to the interventional procedure is used. In choosing the appropriate approach, the duration of the procedure itself is reduced and any unnecessary procedures are also eliminated. More particularly, a detailed 3D geometric representation of the LA and PVs help the electrophysiologist decide how much radiofrequency energy to use at different locations and whether transmural lesions can be delivered without causing excessive delivery of radiofrequency current where it is not desirable, thus making the procedure more efficacious and reducing the risk of complications such as PV stenosis. These features may be further provided automatically or semiwith user input and interaction.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for planning atrial fibrillation (AF) ablation for a patient, the method comprising:
   obtaining cardiac acquisition data from a medical imaging system;
   generating from the acquisition data a cardiac 3D model including the left atrium, left circumflex artery, coronary arteries and pulmonary veins of the patient;
   identifying one or more left atrial (LA) and pulmonary vein (PV) anatomical landmarks on said 3D model and inserting geometric markers therein corresponding to selected ones of said anatomical landmarks;
   generating from the 3D model graphs or plots of muscle thickness in and around the PV ostium;
   performing vessel tracking segmentation of the coronary arteries;
   identifying areas of the left atrium and pulmonary veins within a determined proximity with respect to the left circumflex artery;
   creating a translucent 3D rendering of the LA and PVs along with and in contrast to an opaque rendering of the coronary arteries, and highlighting areas of the LA in proximity of the left circumflex artery (LCx);
   determining from the graphs or plots of muscle thickness and the LCx proximity data levels of ablation to be applied to a given area of one or more LA and PV surfaces to avoid excessive ablation in those areas of the LA in proximity to the LCx;
   wherein the 3D model, translucent rendering, opaque rendering, highlighting, muscle thickness graphs or plots, and LCx proximity data are useful to assist an electrophysiologist to decide how much radiofrequency ablation energy to use at different cardiac locations in a subsequent interventional procedure where the 3D model by using the geometric markers is registerable with a projection image on an interventional system to improve the efficiency of the subsequent interventional procedure and reduce the risk of complications.

2. The method of claim 1, wherein said obtaining acquisition data is implemented with protocols directed for imaging the left atrium and pulmonary veins.

3. The method of claim 2, further comprising utilizing post processing software to process said acquisition data so as to generate immersible views of the left atrium and pulmonary veins.

4. The method of claim 3, wherein said 3D model and said immersible views are visualized through a display screen associated with said interventional system.

5. The method of claim 1, wherein said obtaining acquisition data is EKG gated.

6. A method for planning atrial fibrillation (AF) ablation for a patient, the method comprising:
   obtaining cardiac acquisition data from a medical imaging system using a protocol directed toward the left atrium and pulmonary veins;
   segmenting said acquisition data using a 3D protocol so as to visualize the left atrium and pulmonary veins;
   generating a 3D model of the left atrium, coronary arteries and pulmonary veins of the patient;
   identifying one or more left atrial (LA) and pulmonary vein (PV) anatomical landmarks on said 3D model and inserting geometric markers therein corresponding to selected ones of said anatomical landmarks;
   generating from the 3D model graphs or plots of muscle thickness in and around the PV ostium;
   performing vessel tracking segmentation of the coronary arteries;
   identifying areas of the left atrium and pulmonary veins within a determined proximity with respect to the left circumflex artery;
   creating a translucent 3D rendering of the LA and PVs along with and in contrast to an opaque rendering of the coronary arteries, and highlighting areas of the LA in proximity of the left circumflex artery (LCx);
   determining from the graphs or plots of muscle thickness and the LCx proximity data levels of ablation to be applied to a given area of one or more LA and PV surfaces to avoid excessive ablation in those areas of the LA in proximity to the LCx;
   wherein the 3D model, translucent rendering, opaque rendering, highlighting, muscle thickness graphs or plots, and LCx proximity data are useful to assist an electrophysiologist to decide how much radiofrequency ablation energy to use at different cardiac locations in a subsequent interventional procedure where the 3D model by using the geometric markers is registerable with a projection image on an interventional system to improve the efficiency of the subsequent interventional procedure and reduce the risk of complications.

7. The method of claim 6, further comprising utilizing post processing software to process said acquisition data so as to generate immersible views of the left atrium and pulmonary veins.

8. The method of claim 7, wherein said 3D model and said immersible views are visualized through a display screen associated with said interventional system.

9. The method of claim 6, wherein said obtaining acquisition data is EKG gated.

10. The method of claim 6, wherein said levels of ablation are identified through areas of spectral coloring included in a 3D map.

11. The method of claim 6, wherein said medical imaging system is one of a computed tomography system, a magnetic resonance imaging system and an ultrasound system.

12. A method for planning atrial fibrillation (AF) ablation for a patient, the method comprising:

obtaining acquisition data from a cardiac computed tomography (CT) imaging system using a protocol directed toward the left atrium and pulmonary veins;

segmenting said acquisition data using a 3D protocol so as to visualize the left atrium and pulmonary veins;

generating a 3D model of the left atrium, coronary arteries and pulmonary veins of the patient;

identifying one or more left atrial (LA) and pulmonary vein (PV) anatomical landmarks on said 3D model and inserting geometric markers therein corresponding to selected ones of said anatomical landmarks;

generating from the 3D model graphs or plots of muscle thickness in and around the PV ostium;

performing vessel tracking segmentation of the coronary arteries;

identifying areas of the left atrium and pulmonary veins within a determined proximity with respect to the left circumflex artery;

creating a translucent 3D rendering of the LA and PVs along with and in contrast to an opaque rendering of the coronary arteries, and highlighting areas of the LA in proximity of the left circumflex artery (LCx);

determining from the graphs or plots of muscle thickness and the LCx proximity data levels of ablation to be applied to a given area of one or more LA and PV surfaces to avoid excessive ablation in those areas of the LA in proximity to the LCx;

wherein the 3D model, translucent rendering, opaque rendering, highlighting, muscle thickness graphs or plots, and LCx proximity data are useful to assist an electrophysiologist to decide how much radiofrequency ablation energy to use at different cardiac locations in a subsequent interventional procedure where the 3D model by using the geometric markers is registerable with a projection image on a fluoroscopy system to improve the efficiency of the subsequent interventional procedure and reduce the risk of complications.

13. The method of claim 12 further comprising utilizing post processing software to process said acquisition data so as to generate immersible views of the left atrium and pulmonary veins.

14. The method of claim 13, wherein said 3D model and said immersible views are visualized through a display screen associated with said fluoroscopy system.

15. The method of claim 12, wherein said obtaining acquisition data is EKG gated.

16. The method of claim 12, wherein said levels of ablation are identified through areas of spectral coloring included in a 3D map.

* * * * *

UNITED STATES PATENT AND TRADEMARK OFFICE
CERTIFICATE OF CORRECTION

PATENT NO. : 7,565,190 B2
APPLICATION NO. : 10/249812
DATED : July 21, 2009
INVENTOR(S) : Okerlund et al.

It is certified that error appears in the above-identified patent and that said Letters Patent is hereby corrected as shown below:

On the Title Page, item (75), under "Inventors", in Column 1, Lines 2-3, delete "W305 N2963 Red Oak Ct., Pewaukee, WI (US) 53072;" and insert -- Pewaukee, WI (US); --, therefor.

On Page 2, item (56), under "OTHER PUBLICATIONS", in Column 1, Line 4, delete "descritpoin," and insert -- description, --, therefor.

On Page 2, item (56), under "OTHER PUBLICATIONS", in Column 2, Line 26, delete "Ekectrophysiol," and insert -- Electrophysiol, --, therefor.

On Page 2, item (56), under "OTHER PUBLICATIONS", in Column 2, Line 30, delete "Electrophysioll" and insert -- Electrophysiol --, therefor.

On Page 2, item (56), under "OTHER PUBLICATIONS", in Column 2, Line 66, delete "Clincal" and insert -- Clinical --, therefor.

On Page 3, item (56), under "OTHER PUBLICATIONS", in Column 2, Line 3, delete " ""Usless"" " and insert -- 'Useless' --, therefor.

In Column 1, Line 28, delete "100″ C" and insert -- 100° C --, therefor.

In Column 1, Line 31, delete "70to 80″ C" and insert -- 70 to 80° C --, therefor.

In Column 1, Line 32, delete "50″ C" and insert -- 50° C --, therefor.

UNITED STATES PATENT AND TRADEMARK OFFICE
CERTIFICATE OF CORRECTION

PATENT NO. : 7,565,190 B2
APPLICATION NO. : 10/249812
DATED : July 21, 2009
INVENTOR(S) : Okerlund et al.

It is certified that error appears in the above-identified patent and that said Letters Patent is hereby corrected as shown below:

In Column 4, Line 12, delete "semiwith" and insert -- semiautomatically with --, therefor.

In Column 5, Line 39, delete "semiwith" and insert -- semiautomatically with --, therefor.

Signed and Sealed this

Twenty-ninth Day of September, 2009

David J. Kappos
*Director of the United States Patent and Trademark Office*